(12) United States Patent
Chari et al.

(10) Patent No.: US 7,368,565 B2
(45) Date of Patent: May 6, 2008

(54) METHODS FOR PREPARATION OF CYTOTOXIC CONJUGATES OF MAYTANSINOIDS AND CELL BINDING AGENTS

(75) Inventors: Ravi V. J. Chari, Newton, MA (US); Wayne C. Widdison, Somerville, MA (US)

(73) Assignee: Immunogen Inc., Cambridge, MA (US)

( * ) Notice: Subject to any disclaimer, the term of this patent is extended or adjusted under 35 U.S.C. 154(b) by 450 days.

(21) Appl. No.: 10/161,651

(22) Filed: Jun. 5, 2002

(65) Prior Publication Data

US 2003/0055226 A1    Mar. 20, 2003

Related U.S. Application Data

(62) Division of application No. 09/867,598, filed on May 31, 2001, now Pat. No. 6,441,163.

(51) Int. Cl.
*A61K 39/00* (2006.01)
(52) U.S. Cl. .................. 540/458; 424/184.1
(58) Field of Classification Search ............. 424/184.1
See application file for complete search history.

(56) References Cited

U.S. PATENT DOCUMENTS

| 4,361,650 A | * | 11/1982 | Asai et al. ................. 435/119 |
| 5,208,020 A | * | 5/1993 | Chari et al. .............. 424/181.1 |
| 5,416,064 A | | 5/1995 | Blättler et al. |
| 5,612,474 A | * | 3/1997 | Patel ....................... 536/27.14 |
| 6,316,003 B1 | * | 11/2001 | Frankel et al. ......... 424/196.11 |
| 6,441,163 B1 | * | 8/2002 | Chari et al. ................. 540/458 |
| 6,716,821 B2 | * | 4/2004 | Zhao et al. ................... 514/34 |

FOREIGN PATENT DOCUMENTS

| CA | 2006408 | 6/1990 |
| EP | 0 425 235 A | 5/1991 |
| EP | 1 258 255 A1 | 11/2002 |
| WO | WO 01/24763 A | 4/2001 |
| WO | WO 02/16368 A1 | 2/2002 |
| WO | WO 02/094325 A | 11/2002 |
| WO | WO 03/057163 A | 7/2003 |

OTHER PUBLICATIONS

Pietersz, Geoffrey (Bioconjugate Chemistry 1990; 1: 89-94).*
Lewis et al. (Bioconjugate Chem. 2001; 12: 320-324).*
S. Morris Kupchan, et al., "Structural Requirements for Antileukemic Activity among the Naturally Occurring and Semisynthetic Maytansinoids," 1978, pp. 31-37, Journal of Medicinal Chemistry, vol. 21, No. 1.
Akiyoshi Kawai, et al., "Chemical Modification of Ansamitocins. III. Synthesis and Biological Effects of 3-Acyl Esters of Maytansinol," 1984, pp. 3441-3451, Chemical and Pharmaceutical Bulletin, vol. 32, No. 9.
C Liu, et al. "Cure of human small cell lung cancer xenografts in SCID mice by a hN901-maytansinoid immunoconjugate" *Proceedings of the American Association for Cancer Research Annual Meeting*, vol. 38, No. 0, 1997, p. 29.
Cynthia Ladino, et al. "Folate-maytansinoid: target-selective drugs of low-molecular weight" *International Journal of Cancer*, 73(6), pp. 859-864.
Smith, S, "Technology evaluation: C242-DM1, ImmunoGen Inc," Current Opinion in Molecular Therapeutics; vol. 3 (2), pp. 198-203, 2001; XP-008011026.
Liu, C. et. al., "Eradication of large colon tumor xenografts by targeted delivery of maytansinoids," Proc. Natl. Acad. Aci. USA, vol. 93, pp. 8618-8623, Aug. 1996; XP-002181060.
Chari, R. et al., "Immunoconjugates Containing Novel Maytansinoids: Promising Anticancer Drugs," 6175 Cancer Research, 52(Jan. 1, 2002), No. 1, Baltimore, MD, USA; XP 000453560.

* cited by examiner

*Primary Examiner*—Brandon Fetterolf
(74) *Attorney, Agent, or Firm*—Sughrue Mion, PLLC

(57) ABSTRACT

The present invention discloses a one-step process for the production of cytotoxic conjugates of maytansinoids and cell binding agents. Maytansinoids having a disulfide linker that bears a reactive moiety are linked to cell binding agents, such as antibodies, without prior modification of the cell binding agent. These conjugates are useful as therapeutic agents which are delivered specifically to target cells and are cytotoxic.

17 Claims, 5 Drawing Sheets

DM1, 1

7: R' = H
8a: R' = SO₃⁻Na⁺
8b: R' = SO₃H

2: R' = H
3a: R' = SO₃⁻Na⁺
3b: R' = SO₃H

2: R = H
3a: R = SO₃⁻Na⁺
3b: R = SO₃H

METHODS FOR PREPARATION OF CYTOTOXIC CONJUGATES OF MAYTANSINOIDS AND CELL BINDING AGENTS

This application is a Divisional of U.S. application Ser. No. 09/867,598, filed May 31, 2001 now U.S. Pat. No. 6,441,163 (now allowed).

FIELD OF THE INVENTION

The present invention relates to an improved method for preparing cytotoxic conjugates comprising maytansinoids and cell binding agents. These conjugates have therapeutic use as they are delivered to a specific cell population in a targeted fashion. The present invention also relates to a method for preparing maytansinoids having a disulfide moiety that bears a reactive group which may be used in the preparation of cytotoxic conjugates. The present invention further relates to novel maytansinoids.

BACKGROUND OF THE INVENTION

Many reports have appeared on the attempted specific targeting of tumor cells with monoclonal antibody-drug conjugates (Sela et al. in *Immunoconjugates* 189-216 (C. Vogel, ed. 1987); Ghose et al, in *Targeted Drugs* 1-22 (E. Goldberg, ed. 1983); Diener et al, in *Antibody Mediated Delivery Systems* 1-23 (J. Rodwell, ed. 1988); Pietersz et al, in *Antibody Mediated Delivery Systems* 25-53 (J. Rodwell, ed. 1988); Bumol et al, in *Antibody Mediated Delivery Systems* 55-79 (J. Rodwell, ed. 1988). Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al. *Cancer Res.* 46:2407-2412 (1986); Ohkawa et al. *Cancer Immumol. Immunother.* 23:81-86 (1986); Endo et al. *Cancer Res.* 47:1076-1080 (1980)), dextran (Hurwitz et al. *Appl. Biochem.* 2:25-35 (1980); Manabi et al. *Biochem. Pharmacol.* 34:289-291 (1985); Dillman et al. *Cancer Res.* 46:4886-4891 (1986); Shoval et al. *Proc. Natl. Acad. Sci.* 85: 8276-8280 (1988)), or polyglutamic acid (Tsukada et al. *J. Natl. Canc. Inst.* 73:721-729 (1984); Kato et al. *J. Med. Chem.* 27:1602-1607 (1984); Tsukada et al. *Br. J Cancer* 52:111-116 (1985)).

A wide array of linker technologies has been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (*Biochem. Biophys. Res. Commun.* 102:1048-1054 (1981)). Yang and Reisfeld used the same technique to conjugate daunorubicin to an anti-melanoma antibody (*J. Natl. Canc. Inst.* 80:1154-1159 (1988)). Recently, Dillman et al. also used an acid-labile linker in a similar fashion to prepare conjugates of daunorubicin with an anti-T cell antibody (*Cancer Res.* 48:6097-6102 (1988)).

An alternative approach, explored by Trouet et al. involved linking daunorubicin to an antibody via a peptide spacer arm (*Proc. Natl. Acad. Sci.* 79:626-629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al. *J. Biol. Chem.* 260:12035-12041 (1985); Lambert et al. in *Immunotoxins* 175-209 (A. Frankel, ed. 1988); Ghetie et al. *Cancer Res.* 48:2610-2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al. described the conversion of methotrexate into a mercaptoethylamide derivative followed by conjugation with poly-D-lysine via a disulfide bond (*J. Biol. Chem.* 260:10905-10908 (1985)). In addition, a report described the preparation of a conjugate of the trisulfide-containing toxic drug calicheamycin with an antibody (Menendez et al. Fourth International Conference on Monoclonal Antibody Immunoconjugates for Cancer, San Diego, Abstract 81 (1989)). Another report described the preparation of a conjugate of the trisulfide-containing toxic drug calicheamycin with an antibody (Hinman et al, 53 *Cancer Res.* 3336-3342 (1993)).

One reason for the lack of disulfide linked antibody-drug conjugates is the unavailability of cytotoxic drugs that bear a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin and vincristine. In order to achieve significant cytotoxicity, linkage of a large number of drug molecules either directly to the antibody or through a polymeric carrier molecule becomes necessary. However such heavily modified antibodies often display impaired binding to the target antigen and fast in vivo clearance from the blood stream.

Maytansinoids are highly cytotoxic drugs. Maytansine was first isolated by Kupchan et al. from the east African shrub *Maytenus serrata* and shown to be 100 to 1000 fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al. *J. Med. Chem.* 21:31-37 (1978); Higashide et al. *Nature*

270:721-722 (1977); Kawai et al. Chem. Pharm. Bull. 32:3441-3451 (1984)). Examples of analogues of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters can be classified into two groups:

(a) C-3 esters with simple carboxylic acids (U.S. Pat. Nos. 4,248,870; 4,265,814; 4,308,268; 4,308,269; 4,309,428; 4,317,821; 4,322,348; and 4,331,598), and (b) C-3 esters with derivatives of N-methyl-L-alanine (U.S. Pat. Nos. 4,137,230; 4,260,608; 5,208,020; and *Chem. Pharm. Bull.* 12:3441 (1984)).

Esters of group (b) were found to be much more cytotoxic than esters of group (a).

Maytansine is a mitotic inhibitor. Treatment of L1210 cells in vivo with maytansine has been reported to result in 67% of the cells accumulating in mitosis. Untreated control cells were reported to demonstrate a mitotic index ranging from between 3.2 to 5.8% (Sieber et al. 43 *Comparative Leukemia Research* 1975, Bibl. Haemat. 495-500 (1976)). Experiments with sea urchin eggs and clam eggs have suggested that maytansine inhibits mitosis by interfering with the formation of microtubules through the inhibition of the polymerization of the microtubule protein, tubulin (Remillard et al. *Science* 189:1002-1005 (1975)).

In vitro, P388, L1210, and LY5178 murine leukemic cell suspensions have been found to be inhibited by maytansine at doses of $10^{-3}$ to $10^{-1}$ µg/µl with the P388 line being the most sensitive. Maytansine has also been shown to be an active inhibitor of in vitro growth of human nasopharyngeal carcinoma cells, and the human acute lymphoblastic leukemia line CEM was reported inhibited by concentrations as low as $10^{-7}$ mg/ml (Wolpert-DeFillippes et al. *Biochem. Pharmacol.* 24:1735-1738 (1975)).

In vivo, maytansine has also been shown to be active. Tumor growth in the P388 lymphocytic leukemia system was shown to be inhibited over a 50- to 100-fold dosage range which suggested a high therapeutic index; also significant inhibitory activity could be demonstrated with the L1210 mouse leukemia system, the human Lewis lung carcinoma system and the human B-16 melanocarcinoma system (Kupchan, *Ped. Proc.* 33:2288-2295 (1974)).

Current methods of conjugation of maytansinoids with cell binding agents (such as antibodies) involve two reaction steps. A cell binding agent, for example an antibody, is first modified with a cross-linking reagent such as N-succinimidyl pyridyldithiopropionate (SPDP) to introduce dithiopyridyl groups into the antibody (Carlsson et al. *Biochem. J.* 173:723-737 (1978); U.S. Pat. No. 5,208,020). In a second step, a reactive maytansinoid having a thiol group, such as DM1, is added to the modified antibody, resulting in the displacement of the thiopyridyl groups in the modified antibodies, and the production of disulfide-linked cytotoxic maytansinoid/antibody conjugates (U.S. Pat. No. 5,208,020).

The current methods of conjugation of maytansinoids with antibodies suffer from the drawbacks of subjecting antibodies to two reaction steps, thus requiring two protein purification steps of gel-filtration to separate the proteins from unconjugated small organic molecules such as SPDP and maytansinoids. This makes the methods expensive and time consuming, and also results in low product yield.

Accordingly, a method for conjugating maytansinoids with cell binding agents where the number of reaction steps is reduced, with a concomitant reduction in time and expense, and where the yield is increased, is greatly needed.

SUMMARY OF THE INVENTION

In one embodiment of the invention, a one-step process for the production of cytotoxic conjugates of maytansinoids and cell binding agents is disclosed. Maytansinoids having a disulfide moiety that bears a reactive group are linked to cell binding agents, such as antibodies, without prior modification of the cell binding agent. This conjugation process minimizes the reaction time and processing time for the sensitive antibody protein molecules, and also minimizes the protein purification steps, thus improving the overall yield. These conjugates are useful as therapeutic agents which are delivered specifically to target cells and are cytotoxic.

In a second embodiment, the present invention discloses novel methods for the synthesis of maytansinoids having a disulfide moiety that bears a reactive group. Maytansinoids are organic molecules that are sensitive to aqueous conditions of low (pH 5 and lower) or high pH (pH 8 and higher) and have poor solubilities in aqueous solutions. The novel method disclosed here overcomes these problems by converting maytansinoids to maytansinoids having a disulfide moiety that bears a reactive group, in organic solvents or mixtures of aqueous and organic solvents. The resulting reactive maytansinoid derivatives have better solubilities in aqueous solutions and can be conjugated to cell binding agents in a single reaction step in aqueous buffers under mild conditions (pH 6-8). An additional advantage is that all the maytansinoid intermediates in the process can be fully analyzed before they are conjugated. Synthesis of suitable maytansinoids having a disulfide moiety that bears a reactive group such as compounds 2 and and 3a discussed below, are described.

In a third embodiment of the invention, a method of producing other maytansinoid derivatives, such as compounds 6 and 10, that may be used in the production of maytansinoids having a disulfide moiety that bears a reactive group, such as compounds 2 and 3a, is disclosed.

In a fourth embodiment, several new maytansinoids, compounds 2, 3a, 6, and 10, are described, the uses of which include the production of novel cytotoxic conjugates.

DETAILED DESCRIPTION OF THE INVENTION

Figure 1:
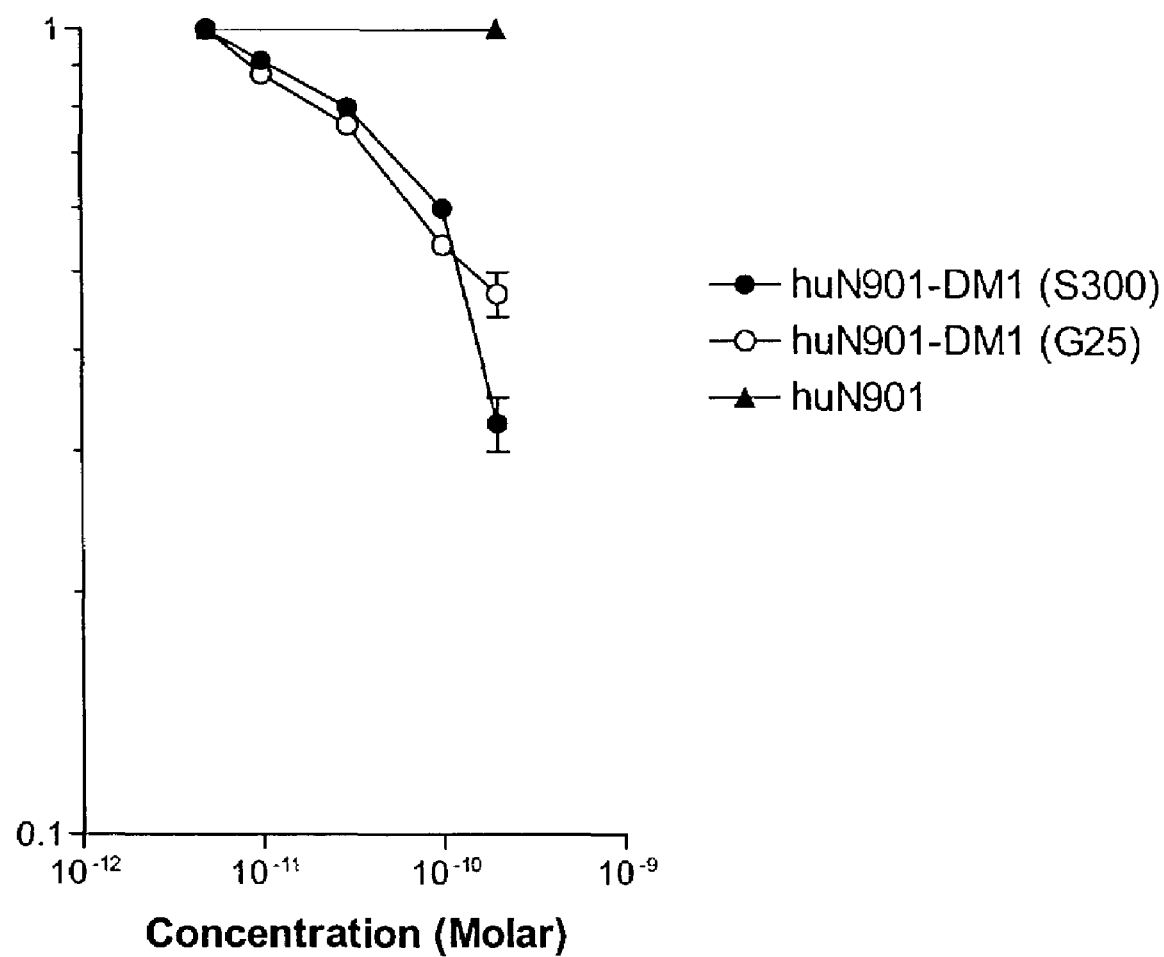
FIG. 1 shows the results of an experiment assaying the ability of huN901-maytansinoid conjugates prepared with 2 by the method of the present invention, followed by purification either by Sephacryl S300 (●) or Sephadex G25 (○) chromatography, and the unconjugated huN901 antibody (▲) to kill antigen positive cells.
Figure 2:
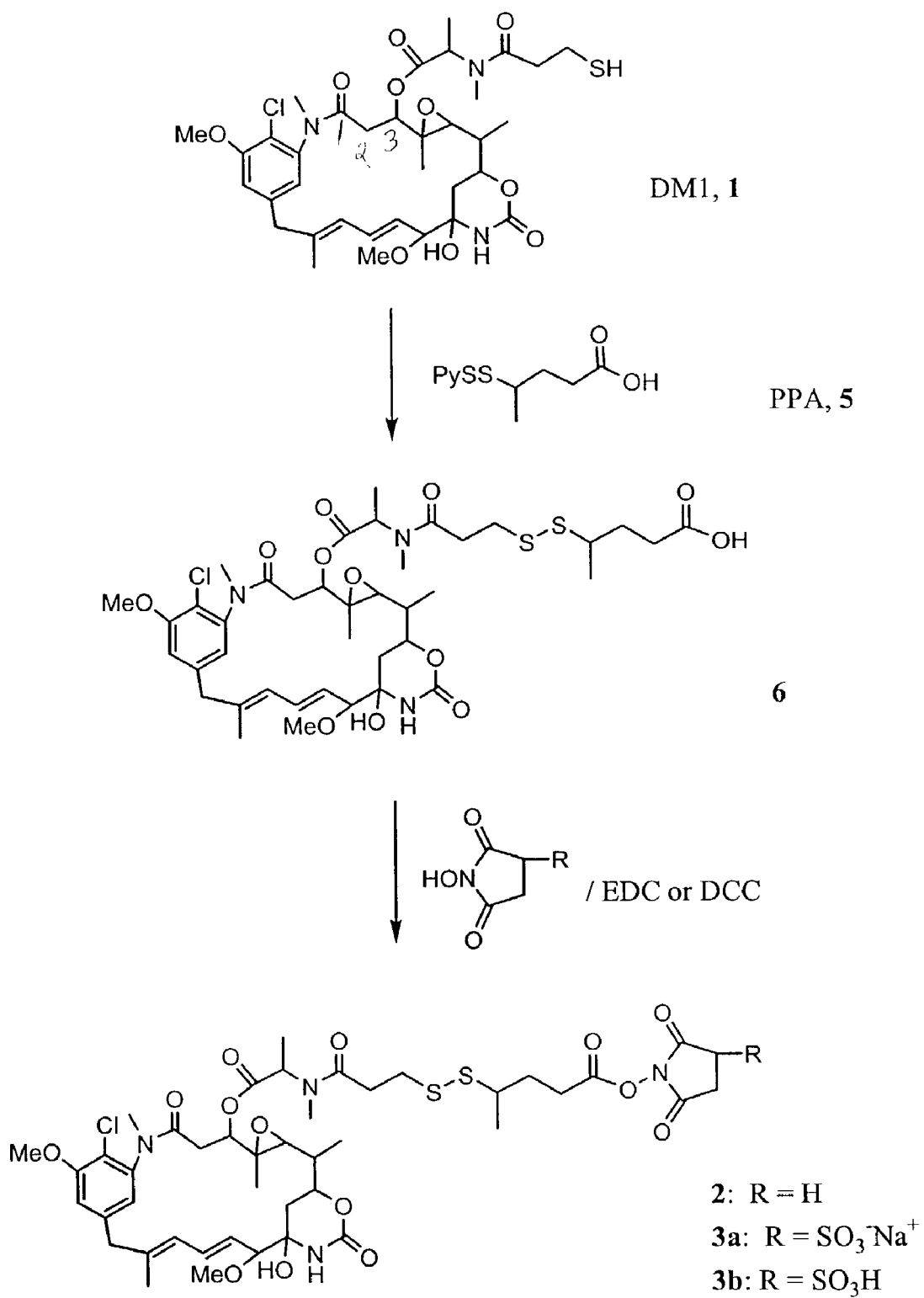
FIG. 2 shows the synthesis pathway of maytansinoids having a disulfide moiety that bears a reactive group.
Figure 3:
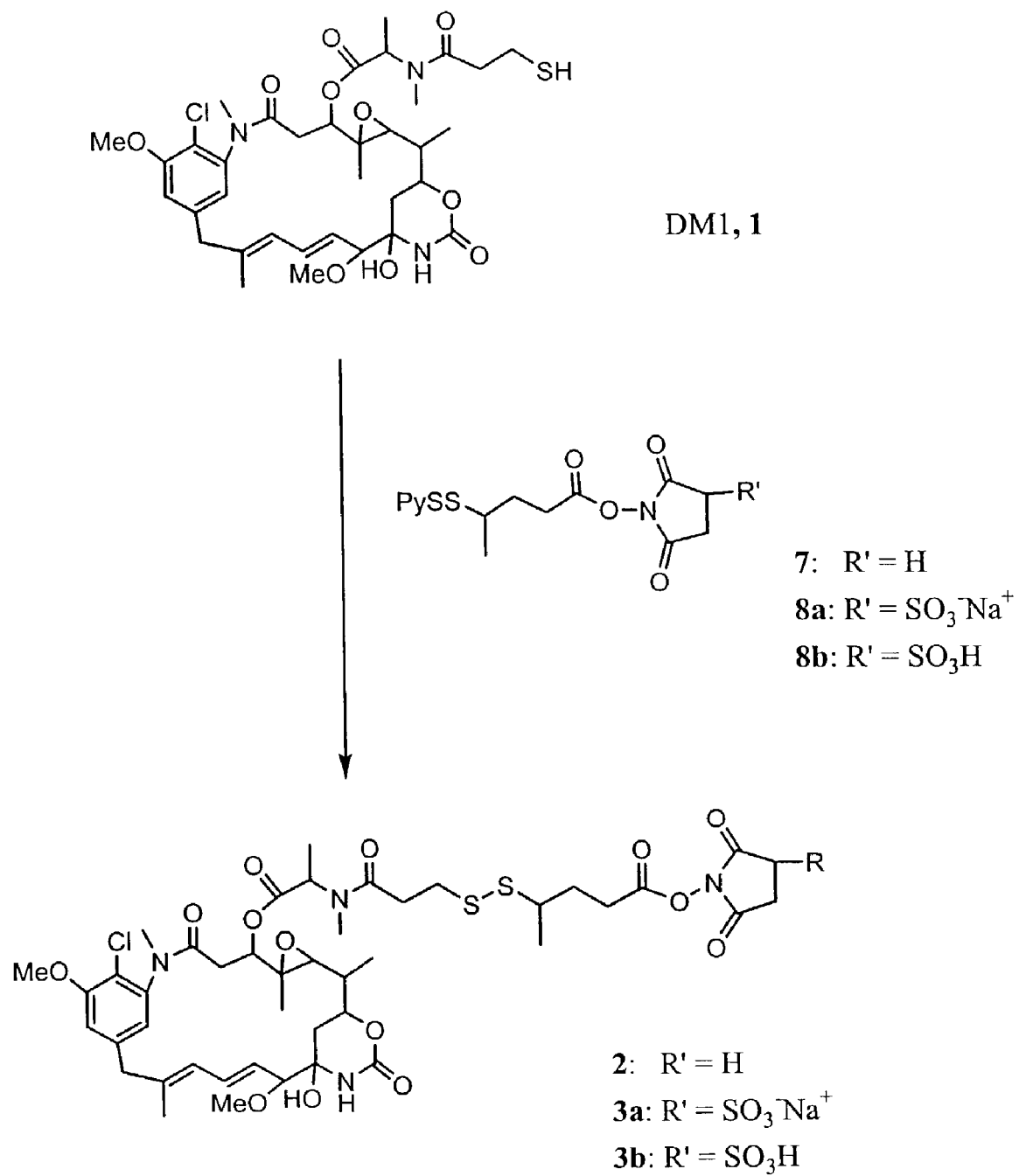
FIG. 3 shows an alternative synthesis pathway of maytansinoids having a disulfide moiety that bears a reactive group.
Figure 4:
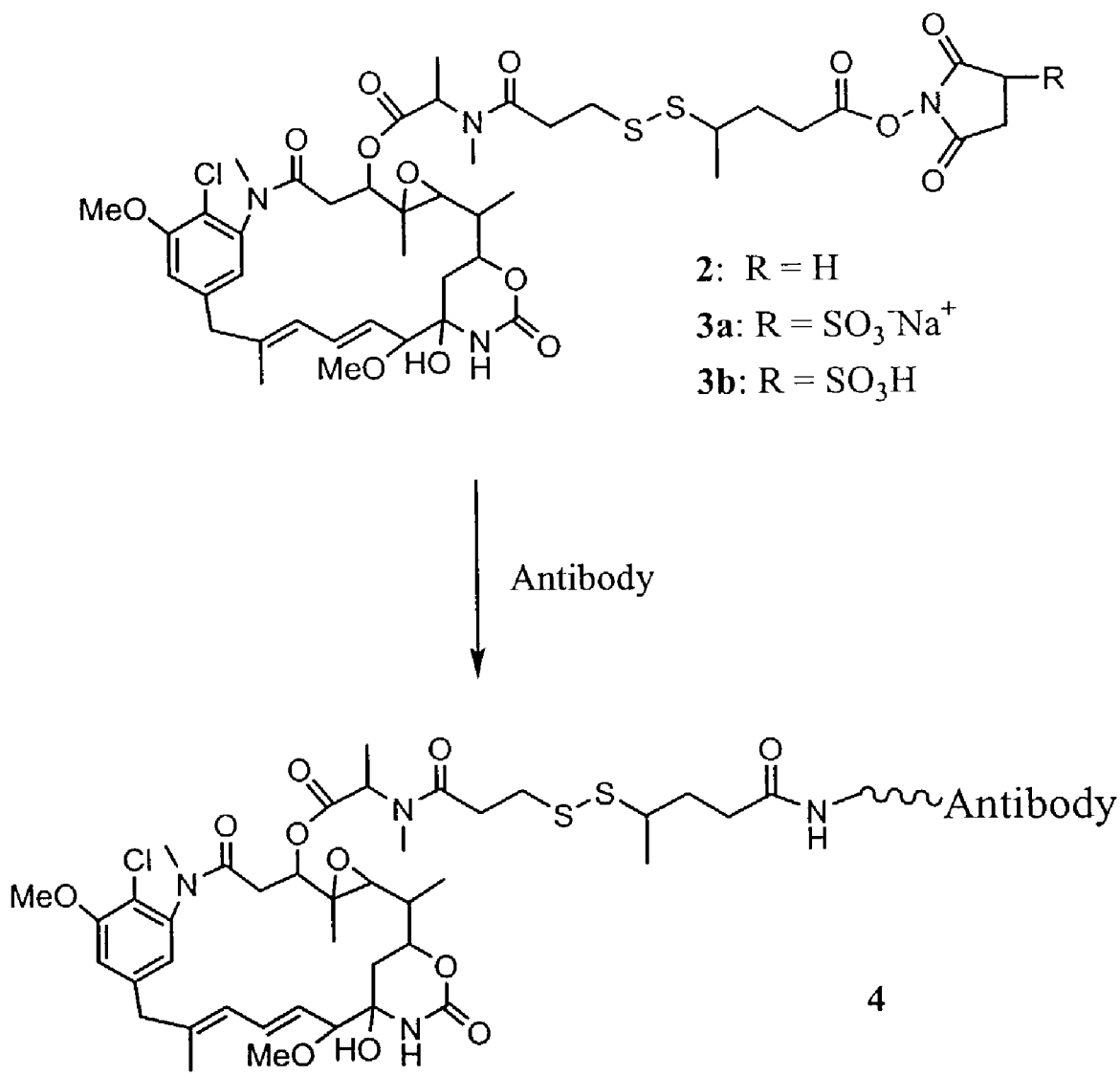
FIG. 4 shows the synthesis pathway of cytotoxic conjugates.

This invention discloses a one-step process for the synthesis of cytotoxic conjugates comprising maytansinoids and cell binding agents. The invention also discloses a process for the synthesis of novel maytansinoids having a disulfide moiety that bears a reactive group, such as compounds 2 and 3a. In addition, this invention describes a process for the synthesis of novel maytansinoid derivatives, such as compounds 6 and 10. This invention further describes novel maytansinoid derivatives, such as compounds 6 and 10, which are useful in the production of maytansinoids having a disulfide moiety that bears a reactive group. This invention also further describes novel maytansinoids having a disulfide moiety that bears a reactive group, such as compounds 2 and 3a, which are useful for the synthesis of novel cytotoxic conjugates.

The art reveals that it is extremely difficult to modify existing drugs without diminishing their cytotoxic potential. The disclosed invention overcomes this problem by teaching a method of modifying maytansinoid molecules with reactive chemical moieties, especially maytansinoid molecules containing a disulfide moiety and a reactive group, which allows linkage to appropriate cell binding agents. As a result, the disclosed novel maytansinoids having a disulfide moiety that bears a reactive group preserve, and in some cases even enhance, the cytotoxic potency of the naturally occurring maytansinoids.

The cytotoxic maytansinoid-cell binding agent conjugates permit the full measure of the cytotoxic action of the maytansinoid derivatives to be applied in a targeted fashion against unwanted cells only, thereby avoiding side effects due to damage to non-targeted healthy cells. Thus, the invention provides useful agents, and novel methods for making the same, for the elimination of diseased or abnormal cells that are to be killed or lysed, such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

Thus, this invention teaches a one-step method for the production of cytotoxic conjugates comprising maytansinoids and cell binding agents. The invention further teaches a method for the synthesis of maytansinoid derivatives, and maytansinoids having a disulfide moiety that bears a reactive group that allows chemical linkage to a cell binding agent while keeping a high cytotoxicity either in bound form or in released form or in both states. Finally, the invention discloses maytansinoid derivatives useful in the production of maytansinoids having a disulfide moiety that bears a reactive group, and maytansinoids having a disulfide moiety that bears a reactive group useful for the synthesis of novel cytotoxic conjugates.

The cytotoxic conjugate according to the present invention comprises one or more maytansinoids linked to a cell binding agent. In order to link the maytansinoid to a cell binding agent, the maytansinoid must first be modified.

Maytansinoids that can be used in the present invention to produce the reactive maytansinoid derivatives capable of being linked to a cell binding agent are well known in the art and can be isolated from natural sources according to known methods or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring include:

(1) C-19-dechloro (U.S. Pat. No. 4,256,746) (prepared by LAH reduction of ansamytocin P2);

(2) C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl (demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from *Nocardia*);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

In order to link the maytansinoid to the cell binding agent, the maytansinoid comprises a linking moiety. The linking moiety contains a chemical bond that allows for the release of fully active maytansinoids at a particular site. Suitable chemical bonds are well known in the art and include disulfide bonds, acid labile bonds, photolabile bonds, peptidase labile bonds and esterase labile bonds. Preferred are disulfide bonds.

According to the present invention, the linking moiety comprises a reactive chemical group. In a preferred embodiment, the reactive chemical group can be covalently bound to the maytansinoid via a disulfide bond linking moiety.

Particularly preferred reactive chemical groups are N-succinimidyl esters and N-sulfosuccinimidyl esters.

Particularly preferred maytansinoids comprising a linking moiety that contains a reactive chemical group are C-3 esters of maytansinol and its analogs where the linking moiety contains a disulfide bond and the chemical reactive group comprises a N-succinimidyl or N-sulfosuccinimidyl ester.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

While the synthesis of esters of maytansinol having a linking moiety is described below in terms of disulfide bond containing linking moieties, one of skill in the art will understand that linking moieties with other chemical bonds (as described above) can also be used with the present invention, as can other maytansinoids. Specific examples of other chemical bonds include acid labile bonds, photolabile bonds, peptidase labile bonds and esterase labile bonds. The disclosure of U.S. Pat. No. 5,208,020, incorporated herein, teaches the production of maytansinoids bearing such bonds.

The synthesis of maytansinoid derivatives and maytansinoids having a disulfide moiety that bears a reactive group can be described by reference to FIGS. 1-4, where disulfide-containing maytansinoid esters are prepared.

Most of the methods of the present invention utilizes thiol-containing maytansinoid (DM1), formally termed $N^{2'}$-deacetyl-$N^{2'}$-(3-mercapto-1-oxopropyl)-maytansine, as the starting reagent. DM1 is represented by the following structural formula (1):

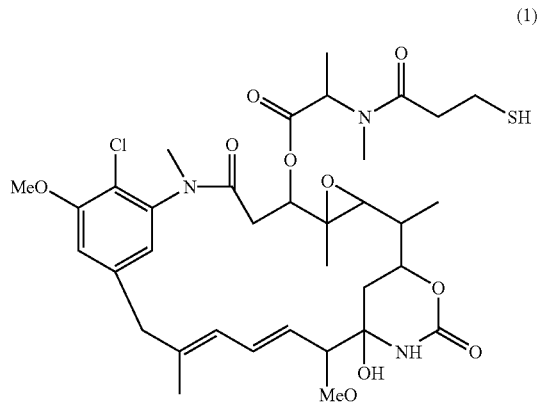

(1)

Production of Cytotoxic Conjugates

Representational cytotoxic conjugates of the invention are antibody/maytansinoid, antibody fragment/maytansinoid, epidermal growth factor (EGF)/maytansinoid, melanocyte stimulating hormone (MSH)/maytansinoid, thyroid stimulating hormone (TSH)/maytansinoid, estrogen/maytansinoid, estrogen analogue/maytansinoid, androgen/maytansinoid, and androgen analogue/maytansinoid.

The reactive group containing maytansinoid is reacted with a cell binding agent to produce cytotoxic conjugates. These conjugates may be purified by HPLC or by gel-filtration.

Scheme 1: More specifically, a solution of an antibody in aqueous buffer may be incubated with a molar excess of maytansinoids having a disulfide moiety that bears a reactive group. The reaction mixture can be quenched by addition of excess amine (such as ethanolamine, taurine, etc.). The maytansinoid-antibody conjugate may then be purified by gel-filtration.

The number of maytansinoid molecules bound per antibody molecule can be determined by measuring spectrophotometrically the ratio of the absorbance at 252 nm and 280 nm. An average of 1-10 maytansinoid molecules/antibody molecule can be linked by this method.

Conjugates of cell binding agents with maytansinoid drugs of the invention can be evaluated for their ability to suppress proliferation of various unwanted cell lines in vitro. For example, cell lines such as the human epidermoid carcinoma line A-431, the human small cell lung cancer cell line SW2, the human breast tumor line SKBR3 and the Burkitt's lymphoma line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

Production of Maytansinoids Having a Disulfide Moiety that Bears a Reactive Group The novel maytansinoids having a disulfide moiety that bears a reactive group disclosed in the present invention are those compounds represented by formula 11:

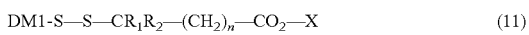

$$DM1-S-S-CR_1R_2-(CH_2)_n-CO_2-X \qquad (11)$$

where $R_1$ and $R_2$ are each independently H, $CH_3$, $C_2H_5$, linear or branched higher alkyl, where n is 1-5, and where X is a part of an active ester, and can be N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, or 3-carboxy-4-nitrophenyl.

Examples of linear alkyls include propyl, butyl, pentyl and hexyl.

Examples of branched alkyls include isopropyl, isobutyl, sec.-butyl, tert.-butyl, isopentyl and 1-ethyl-propyl.

Preferred embodiments of formula 11 include those maytansinoids having a disulfide moiety that bears a reactive $CO_2$—X ester, where X is N-succinimidyl or N-sulfosuccinimidyl. More preferred embodiments of formula 11 include those maytansinoids having a disulfide moiety that bears a reactive group where $R_1$ is H, $R_2$ is $CH_3$, n is 2, and $CO_2$—X is an active N-succinimidyl ester (compound 2) or $CO_2$—X is an active N-sulfosuccinimidyl ester (compound 3a).

Novel maytansinoids having a disulfide moiety that bears a reactive group may be prepared by the following newly disclosed methods.

Scheme 2a: The maytansinoid having a disulfide moiety that bears a reactive N-succinimidyl ester (compound 2) may be prepared by the reaction of $N^{2'}$-deacetyl-$N^{2'}$-[3-(3-carboxy-1-methyl-propyldithio)-1-oxopropyl]-maytansine (compound 6) with N-hydroxysuccinimide in a dry organic solvent in the presence of 1-[3-(dimethylamino)propyl]-3-ethylcarbodiimide.HCl (EDC.HCl) at ambient temperature for approximately 1-12 h. The completion of the reaction may be monitored with standard chemical techniques such as thin layer chromatography (TLC) or high performance liquid chromatography (HPLC). Following the completion of reaction, the maytansinoid derivative having a disulfide moiety that bears a reactive N-succinimidyl ester (compound 2) may be purified using silica gel chromatography or HPLC. Condensing agents other than EDC.HCl may also be employed for the reaction, such as N,N'-dicyclohexylcarbodiimide (DCC).

Scheme 2b: The maytansinoid having a disulfide moiety that bears a reactive N-succinimidyl ester (compound 2) may be prepared by an alternative method. A solution of N-succinimidyl 4-(2-pyridyldithio)-pentanoate (SPP) (compound 7) in methanol is treated with a solution of DM1 in methanol. Sodium acetate buffer (pH 3-5) is added, and the reaction mixture is stirred under an argon atmosphere at room temperature. The progress of the reaction may be monitored by HPLC using a Vydac C-18 column. The product 2 may be purified by HPLC.

Scheme 3a: The maytansinoid having a disulfide moiety that bears a reactive N-sulfosuccinimidyl ester (compound 3a) may be prepared by the reaction of $N^{2'}$-deacetyl-$N^{2'}$-[3-(3-carboxy-1-methyl-propyldithio)-1-oxopropyl]-maytansine (compound 6) with N-hydroxysulfosuccinimide sodium salt (1-2-fold molar excess over acid (6)) in a dry organic solvent (such as methylene chloride, dimethylformamide, tetrahydrofuran, dioxane, diethylether) in the presence of 1-[3-(dimethylamino)propyl]-3-ethylcarbodiimide-.HCl (EDC.HCl) (1-2-fold molar excess over acid (6)). Completion of reaction may be monitored using standard chemical techniques such as TLC or HPLC. Following the completion of the reaction, the maytansinoid derivative having a disulfide moiety that bears a reactive N-sulfosuccinimidyl ester (compound 3a) may be purified by silica gel chromatography, or by HPLC, or by precipitation by addition of large volumes of ethyl acetate (similar to the general method of preparation of N-sulfosuccinimidyl esters as described by Staros, *Biochemistry,* 1982, 21:3950-3955). Condensing agents other than EDC.HCl can be employed for the reaction.

Scheme 3b: The maytansinoid having a disulfide moiety that bears a reactive N-sulfosuccinimidyl ester (compound 3a) may be prepared by an alternative method. A solution of N-sulfosuccinimidyl 4-(2-pyridyldithio)-pentanoate (sulfo-SPP) in methanol is treated with a solution of DM1 in methanol. Sodium acetate buffer (pH 3-5) is added, and the reaction mixture is stirred under an argon atmosphere at room temperature. The progress of the reaction may be monitored by HPLC. The product 3a may be purified by HPLC.

Production of Maytansinoid Derivatives

Schemes 4a and 4b disclose novel methods for the production of a maytansinoid derivative from DM1 (1). This maytansinoid derivative 6 is formally termed $N^{2'}$-deacetyl-$N^{2'}$-[3-(3-carboxy-1-methyl-propyldithio)-1-oxopropyl]-maytansine and represented by the formula:

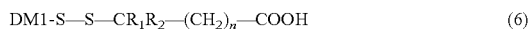

$$\text{DM1-S—S—CR}_1\text{R}_2\text{—(CH}_2)_n\text{—COOH} \qquad (6)$$

$R_1$=H, $R_2$=CH$_3$, n=2.

Maytansinoid derivative 6 may be used directly in the preparation of a number of cytotoxic maytansinoid-cell binding agent conjugates. Preferably, maytansinoid derivative 6 is used in the production of novel maytansinoids having a disulfide moiety that bears a reactive group, using the novel methods set forth above in Schemes 2a and 3a.

Scheme 4a: Maytansinoid derivative 6 may be synthesized by disulfide exchange between DM1 and 4-(2-pyridyldithio)-pentanoic acid (compound 5). A solution of 4-(2-pyridyldithio)-pentanoic acid in methanol is treated with a solution of DM1 in methanol. Potassium phosphate buffer is added, and the reaction mixture is stirred under an argon atmosphere at room temperature. The progress of the reaction may be monitored by HPLC. The product 6 may be purified by HPLC. The purified product may be re-analyzed by HPLC. The identity of the product may be established by high resolution mass spectrometry of the sodium salt of 6.

Scheme 4b: Maytansinoid derivative 6 may be prepared by an alternative method wherein maytansinol is coupled with the mixed disulfide of N-methyl-N-(3-mercaptopropanoyl)-L-alanine and trimethylsilylethyl 4-mercaptopentanoate (compound 9) to yield the maytansinoid ester (compound 10), which is then deprotected to yield compound 6.

Preparation of Cell Binding Agents

The effectiveness of the compounds of the invention as therapeutic agents depends on the careful selection of an appropriate cell binding agent. Cell binding agents may be of any kind presently known, or that become known and include peptides and non-peptides. Generally, these can be antibodies (especially monoclonal antibodies), lymphokines, hormones, growth factors, vitamins, nutrient-transport molecules (such as transferrin), or any other cell binding molecule or substance.

More specific examples of cell binding agents that can be used include:

polyclonal antibodies;

monoclonal antibodies;

fragments of antibodies such as Fab, Fab', and F(ab')$_2$, Fv (Parham, *J. Immunol.* 131:2895-2902 (1983); Spring et al. *J.*

*Immunol.* 113:470-478 (1974); Nisonoff et al. *Arch. Biochem. Biophys.* 89:230-244 (1960));

interferons (e.g. alpha., beta., gamma.);

lymphokines such as IL-2, IL-3, IL-4, IL-6;

hormones such as insulin, TRH (thyrotropin releasing hormone), MSH (melanocyte-stimulating hormone), steroid hormones, such as androgens and estrogens;

growth factors and colony-stimulating factors such as EGF, TGF-alpha, FGF, VEGF, G-CSF, M-CSF and GM-CSF (Burgess, *Immunology Today* 5:155-158 (1984));

transferrin (O'Keefe et al. *J. Biol. Chem.* 260:932-937 (1985)); and vitamins, such as folate.

Monoclonal antibody techniques allow for the production of extremely specific cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may humanized antibodies.

Selection of the appropriate cell binding agent is a matter of choice that depends upon the particular cell population that is to be targeted, but in general human monoclonal antibodies are preferred if an appropriate one is available.

For example, the monoclonal antibody J5 is a murine IgG$_{2a}$ antibody that is specific for the Common Acute Lymphoblastic Leukemia Antigen (CALLA) (Ritz et al. *Nature* 283:583-585 (1980)) and can be used if the target cells express CALLA such as in the disease of acute lymphoblastic leukemia. Similarly, the monoclonal antibody anti-B4 is a murine IgG$_1$, that binds to the CD19 antigen on B cells (Nadler et al. *J. Immunol.* 131:244-250 (1983)) and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myclogenous leukemia. IL-2 which binds to activated T-cells can be used for prevention of transplant graft rejection, for therapy and prevention of graft-versus-host disease, and for treatment of acute T-cell leukemia. MSH which binds to melanocytes can be used for the treatment of melanoma.

Cancers of the breast and testes can be successfully targeted with estrogen (or estrogen analogues) or androgen (or androgen analogues) respectively as cell binding agents.

EXAMPLES

The invention will now be illustrated by reference to non-limiting examples. Unless otherwise stated, all percents, ratios, parts, etc. are by weight. The examples described below are molecules where $R_1$ is H, $R_2$ is CH$_3$, and n is 2. Similar synthesis can be carried out for other molecules where $R_1$ and $R_2$ are each independently H, CH$_3$, C$_2$H$_5$, or higher alkyl; and where n is 1-5.

Example 1a

Preparation of Cytotoxic Conjugates Using Maytansinoid 2

A solution of huN901 antibody (2.5 mg/mL) in aqueous buffer (50 mM potassium phosphate, 50 mM sodium chloride, 2 mM ethylenediaminetetraacetic acid disodium salt), pH 6.5, was incubated with a 6-fold molar excess of maytansinoid 2 in dimethylacetamide (DMA) to give a final DMA concentration of 20%. The reaction was allowed to proceed for 13 h at ambient temperature. The reaction mixture was split into two portions. One portion was purified by passage over a Sephadex G25 gel filtration column, and the second portion was purified over a Sephacryl S300 gel filtration column. In each case the fractions containing monomeric conjugate were pooled. The concentration of the conjugate was determined spectrophotometrically using the known extinction coefficients for the antibody and DM1 components at 280 and 252 nM (for huN901: $\epsilon_{280nm}$=217,560 M$^{-1}$ cm$^{-1}$ and $\epsilon_{252nm}$=80,062 M$^{-1}$ cm$^{-1}$; for DM1 $\epsilon_{280nm}$=5,700 M$^{-1}$ cm$^{-1}$ and $\epsilon_{252nM}$=26,790 M$^{-1}$ cm$^{-1}$).

Purification by Sephadex G25 chromatography gave a conjugate containing, on the average, 2.08 DM1 molecules linked per antibody molecule (yield based on starting antibody=60%). Purification by Sephacryl S300 chromatography gave a conjugate containing, on the average, 1.61 DM1 molecules linked per antibody molecule (yield based on starting antibody=64%).

Example 1b

Preparation of Cytotoxic Conjugates Using Maytansinoid 3a

A solution of huN901 antibody (2.5 mg/mL) in aqueous buffer (50 mM potassium phosphate, 50 mM sodium chloride, 2 mM ethylenediaminetetraacetic acid disodium salt), pH 6.5, was incubated with a 12-fold molar excess of maytansinoid 3a in dimethylacetamide (DMA) to give a final DMA concentration of 20%. The reaction was allowed to proceed for 11 h at ambient temperature. The reaction mixture was split into two portions. One portion was purified by passage over a Sephadex G25 gel filtration column, and the second portion was purified over a Sephacryl S300 gel filtration column. In each case the fractions containing monomeric conjugate were pooled. The concentration of the conjugate was determined spectrophotometrically using the known extinction coefficients for the antibody and DM1 components at 280 and 252 nM (for huN901: $\epsilon_{280nm}$=217,560 M$^{-1}$ cm$^{-1}$ and $\epsilon_{252nm}$=80062 M$^{-1}$ cm$^{-1}$, and for DM1 $\epsilon_{280nm}$=5700 M$^{-1}$ cm$^{-1}$ and $\epsilon_{252nm}$=26790 M$^{-1}$ cm$^{-1}$).

Purification by Sephadex G25 chromatography gave a conjugate containing, on the average, 4.89 DM1 molecules linked per antibody molecule (yield based on starting antibody=59%). Purification by Sephacryl S300 chromatography gave a conjugate containing, on the average, 4.16 DM1 molecules linked per antibody molecule (yield based on starting antibody=58%).

Example 2a

Synthesis of the Maytansinoid Derivative (2) that Bears a Reactive N-succinimidyl Ester All reactions were conducted under an argon atmosphere. All reagents were purchased from the Aldrich Chemical Co., New Jersey. Nuclear Magnetic Resonance ($^1$H NMR) spectra were acquired on a Bruker 400 MHz instrument and mass spectra were acquired on a Bruker Daltonics Esquire 3000 instrument using electrospray ionization.

The syntheses of thiol-containing maytansinoid (L-DM1, 1) has been previously described (U.S. Pat. No. 5,208,020).

Preparation of 4-(2-pyridyldithio)-pentanoic acid (PPA, 5): A 1 L two-necked flask was equipped with a stir bar, an addition funnel and a thermometer. The flask was charged with 150 g of 1,3-dibromobutane (0.74 mol) and 700 mL of dimethyl sulfoxide. A solution of sodium cyanide (37.5 g, 0.76 mol) in deionized water (79 mL) was added dropwise at a rate which did not allow the reaction temperature to exceed 65° C. After addition was complete the reaction was stirred overnight. The mixture was diluted with 700 mL of deionized water and extracted with a 1:1 solution of ethyl acetate:hexanes (2×1.4 L). The organic layers were combined and washed sequentially with 700 mL deionized water and 700 mL saturated aqueous sodium chloride. The solvent was evaporated under reduced pressure (~15 Torr). The residue was dissolved in 210 mL of reagent grade ethanol and transferred to a 1 L flask. Deionized water (210 mL) and thiourea (66.4 g, 0.87 mol) were then added to the flask. The flask was equipped with a reflux condenser and was heated in an oil bath with stirring to give a mild reflux. After 4 hours the oil bath was removed and the flask was allowed to cool to room temperature. A solution of 10 M sodium hydroxide (500 mL) was added and the mixture was heated with an oil bath to a mild reflux with stirring overnight. The oil bath was removed and the flask was allowed to cool to room temperature. The solution was transferred to a separatory funnel and washed twice with 500 mL portions of ethyl acetate. The aqueous layer was transferred to a 2 L flask and cooled in an ice/water bath. Ethyl acetate (1 L) was added and the contents were rapidly stirred as concentrated HCl was added until the aqueous layer tested to be approximately pH 2. The ethyl acetate layer was separated, and the aqueous layer was extracted with ethyl acetate (2×1 L). The organic layers were combined and concentrated by rotary evaporation at room temperature to give 4-mercapto-pentanoic acid, which was used in the next step without further purification.

A 2 L flask containing a stir bar was charged with 2-2'-dithiodipyridine (300 g, 1.36 mol), reagent grade ethanol (1 L) and glacial acetic acid (42 mL). A solution of the crude 4-mercapto pentanoic acid in ethyl acetate (400 mL) was added dropwise over 15 minutes and the reaction was stirred under argon for an additional 2 hours. The solvent was removed by rotary evaporation and the residue was taken up in a minimum of ethyl acetate and purified by column chromatography using a silica gel column (6.25×27 cm). The column was eluted with 4:1 hexanes:ethyl acetate until all of the unreacted 2,2'-dithiopyridine (Aldrithiol-2) was removed. The column was then eluted with 4:1 hexanes:ethyl acetate containing 2% acetic acid. The elution was monitored by TLC and fractions were combined. The solvent was then removed by rotary evaporation under reduced pressure to give pure 4-(2-pyridyldithio)-pentanoic acid (PPA, 5) as a white solid (40 g, 23% overall yield). $^1$H NMR (CDCl$_3$) δ 1.39 (d, 3H), 2.0 (t, 2H), 2.56 (t, 2H), 2.8-3.3 (m, 1H), 6.8-7.2 (m, 1H), 7.6-7.8 (m, 2H), 8.4-8.6 (m, 1H), 11.68 (s 1H).

Preparation of N$^{2'}$-deacetyl-N$^{2'}$-[3-(3-carboxy-1-methyl-propyldithio)-1-oxopropyl]-maytansine (L-DM1-TPA, 6): A solution of 4-(2-pyridyldithio)-pentanoic acid (5, 24 mg, 0.10 mmol) and L-DM1 (1, 30 mg, 0.041 mmol) in glass distilled methanol (5 mL) was vigorously stirred, and 3 mL of an aqueous buffer (200 mM KH$_2$PO$_4$, 2 mM EDTA, pH 7.6) was added dropwise. The reaction was left overnight and product was purified by HPLC using a Vydac C-18, 10×250 mm column, 30° C., flow rate 4.75 mL/min with a linear gradient of acetonitrile (15% to 85% over 30 min) in 40 mM ammonium acetate buffer, pH 7.2. L-DM1-TPA (6) eluted with a retention time of 12 min. The product was collected as the ammonium salt and was taken up in 15 mL of ethyl acetate. The solution was washed successively with 4 mL of 1 M HCl followed by 3 mL of saturated sodium chloride. The organic layer was dried over anhydrous sodium sulfate and solvent was removed under vacuum to give 15 mg (37% yield) of the product 6. The identity of the product was established by high resolution mass spectrometry: calculated for the sodiated molecular ion=892.2891, Found=892.2955. H$^1$ NMR (400 MHz, CDCl$_3$) δ 6.84 (d, 1H, J=1 Hz), 6.76 (dd, 1H, J=7, 1 Hz), 6.59(dd, 1H, J=14,11 Hz), 6.32-6.64 (m, 2H), 5.6-5.7 (m, 1H), 5.13-5.23 (m, 1H), 4.83 (dt, 1H, J=9,3 Hz), 4.31 (dd, 1H, J=12,1 Hz), 3.99 (s, 3H), 3.63 (dd, 1H, J=13,1 Hz), 3.49 (d, 1H, J=9 Hz), 3.36 (s, 3H), 3.22 (d, 3H, J=1 Hz), 3.12 (dd, 1H, J=12,1 Hz), 2.75-2.91 (m, 5H) 2.54-2.72(m, 4H), 2.34-2.52 (m, 2H), 2.20 (dd, 3H, J=13,1 Hz), 1.7-1.9 (m, 4H), 1.66 (s, 3H), 1.42-1.5 (m, 2H), 1.37 (dd, 3H, J=9,1 Hz), 1.2-1.3 (m, 7H), 0.81 (s, 3H).

Preparation of N$^{2'}$-deacetyl-N$^{2'}$-[3-(3-carboxy-1-methyl-propyldithio)-1-oxopropyl]-maytansine N-succinimidyl ester (L-DM1-TPA succinimidyl ester, 2): A solution of L-DM1-TPA (6) (10 mg, 0.011 mmol) in methylene chloride (1.5 mL) was treated with N-hydroxysuccinimide (10 mg, 0.086 mmol) and 1-[3-(dimethylamino)propyl]-3-ethylcarbodiimide.HCl (21 mg, 0.11 mmol) with vigorous stirring. The reaction proceeded for 2 hours after which approximately half of the solvent was removed under vacuum. The remaining solution was subjected to preparative thin layer chromatography (two 2000 micron thick silica plates) using a mobile phase of (methylene chloride:methanol 95:5). The band for desired product (2) was scrapped from the plate and stirred with 20 mL of (methylene chloride:methanol 80:20) and vacuum filtered through a sintered glass funnel. The filtrate was concentrated under vacuum to give (8 mg, 0.0083 mmol, 75% yield) of product. Mass spectral analysis gave a base peak ion consistent with M$^+$+Na 989.4. Fragmentation of the 989.4 ion gave daughter ions, which were also consistent with the structure of 2. H$^1$ NMR (400 MHz, CDCl$_3$) δ 6.96 (d, 1H, J=1.8 Hz), 6.81 (d, 1H, J=1.8 Hz), 6.48 (dd, 1H, J=15,11 Hz), 6.27 (s, 1H), 6.14 (d, 1H, J=11 Hz), 5.53 (dd, 1H, J=15, 9.3 Hz), 5.41 (q, 1H, J=6.9 Hz), 4.36 (dd, 1H, J=12,1 Hz), 3.99 (s, 3H), 3.66 (s, 1H), 3.54 (d, 1H, J=9.3 Hz), 3.4-3.54 (m, 5H), 3.36 (s, 3H), 3.35 (s, 3H), 3.21 (s,3H), 3.12 (d, 1H, J=12.7 Hz), 2.88 (d, 1H, J=5.4 Hz), 2.7 (s, 4H), 2.5-2.65 (m, 5H), 2.1 (d, 1H, J=9.4 Hz), 1.69 (s, 3H), 1.45-1.55 (m, 2H), 1.1-1.3 (m, 10H), 0.83 (s, 3H).

Example 2b

Alternative Method for the Synthesis of the Maytansinoid Derivative (2) that Bears a Reactive N-succinimidyl Ester Preparation of N-succinimidyl ester of 4-(2-pyridyldithio)-pentanoic acid (SPP, 7): A solution of 4-(2-pyridyldithio)-pentanoic acid (5, 30 g, 123 mmol) in methylene chloride (525 mL) was treated with N-hydroxysuccinimide (14.3 g, 124 mmol) and 1-[3-(dimethylamino)propyl]-3-ethylcarbodiimide.HCl (31.8 g, 165 mmol). The contents were stirred at room temperature for 2 hours after which 750 mL of ethyl acetate was added. The solution was washed with 0.5% aqueous acetic acid (3×350 mL) and once with 150 mL of saturated aqueous sodium chloride. The organic layer was dried over anhydrous sodium sulfate, filtered, and the solvent was removed under vacuum by rotary evaporation. The residue was taken up in a minimum volume of ethyl acetate and loaded on a 6.25×20 cm silica column, slurry packed in 1:1 hexanes:ethyl acetate. The column was eluted with 1:1 hexanes:ethyl acetate. Fractions containing the product were combined and solvent was removed by rotary evaporation. The resulting oil (31 g) was taken up in a minimum volume of warm reagent grade ethanol and magnetically stirred as 350 mL of ethyl ether was added, followed by 100 mL of hexanes. The resulting precipitate was collected by vacuum filtration and dried in a vacuum oven at 30 degrees C. for 12 hours, giving 18.7 g of SPP (7) as a white solid (18.7 g, 45% yield). $^1$H NMR (CDCL3) δ 1.39 (d, 3 H), 2.0 (t, 3H), 2.56-3.4 (m, 7 H), 6.8-7.2 (m, 1 H), 7.6-7.8 (m, 2H), 8.4-8.6 (d, 1H). Elemental analysis: Calculated: % C 49.4, % H 4.70, % N 8.20, % S 18.80. Found: % C 49.3% H 4.68, % N 8.18, % S 18.94.

Preparation of N$^{2'}$-deacetyl-N$^{2'}$-[3-(3-carboxy-1-methyl-propyldithio)-1-oxopropyl]-maytansine N-succinimidyl ester (L-DM1-TPA succinimidyl ester, 2): A solution of N-succinimidyl ester of 4-(2-pyridyldithio)-pentanoic acid (SPP, 7, 3 mg, 15 μmol) in methanol (15 ml) was reacted with DM1 (1, 0.58 mg, 0.8 μmol) in dimethylacetamide (0.1 ml). Potassium phosphate buffer (0.5 ml of a 0.2 M solution, pH 6, 2 mM EDTA) was added, and the reaction mixture was stirred under an argon atmosphere at room temperature. The progress of the reaction was monitored by silica gel TLC and the product was purified by preparatory silica gel TLC as described above.

Example 3a

Synthesis of the Maytansinoid Derivative (3a) that Bears a Reactive N-sulfosuccinimidyl Ester Preparation of N$^{2'}$-deacetyl-N$^{2'}$-[3-(3-carboxy-1-methyl-propyldithio)-1-oxopropyl]-maytansine N-sulfosuccinimidyl ester (L-DM1-TPA sulfosuccinimidyl ester, 3a): L-DM1-TPA (6, 2 mg 0.002 mmol) was dissolved in dimethylacetamide (0.25 mL), to which N-hydroxysulfosuccinimide sodium salt (1.0 mg, 0.0046 mmol) and dicyclohexylcarbodiimide (1.0 mg, 0.0048 mmol) were added. After 3 hours, 0.5 mL of diisopropyl alcohol was added and the resulting precipitate was removed by filtration. HPLC analysis (Vydac C-18 column, 10×250 C18 column, 30° C., flow rate 4.75 mL/min, 50 mM triethylammonium formate pH 3.8 buffer with a linear methanol gradient (30% to 90% over 30 minutes) of the filtrate showed two major peaks, one for unreacted L-DM1-TPA at 22 min and one for L-DM1-TPA sulfosuccinimidyl ester at 19 min. The compound eluting at 19 min was isolated and analyzed by mass spectrometry showing that it had the expected peak consistent with the disodiated molecular ion ($M^+ + 2Na$) of 3a, m/e 1091.4. Further fragmentation of the 1091.4 ion gave predictable daughter ions, m/e 1073.4 ($M^+ + 2Na - H_2O$), 874.4 ($M^+ + 2Na$-sodiated N-hydroxysulfosuccinimide).

The preparation of $N^{2'}$-deacetyl-$N^{2'}$-[3-(3-carboxy-1-methyl-propyldithio)-1-oxopropyl]-maytansine (L-DM1-TPA, 6) and 4-(2-pyridyldithio)-pentanoic acid (PPA, 5) were as set forth in EXAMPLE 2a above.

Example 3b

Alternative Method for the Synthesis of the Maytansinoid Derivative (3a) that Bears a Reactive N-sulfosuccinimidyl Ester Maytansinoid 3a can also be prepared directly by reaction of DM1 (1) with the sodium salt of sulfoSPP (N-sulfosuccinimidyl ester of 4-(2-pyridyldithio)-pentanoic acid). The sodium salt of sulfoSPP (8a) can be prepared by coupling of PPA (5) with the sodium salt of N-hydroxysulfosuccinimde in the presence of EDC.HCl, by the method described for SPP (7) (see Example 2a above). Reaction of DM1 with a 20-fold molar excess of 8a in dimethylacetamide and potassium phosphate buffer pH 6 containing 2 mM EDTA at ambient temperature gives maytansinoid 3a, which can be purified by HPLC as described in Example 3a.

Example 4

Alternative Method for the Synthesis of Maytansinoid Derivative (6)

Figure 5:
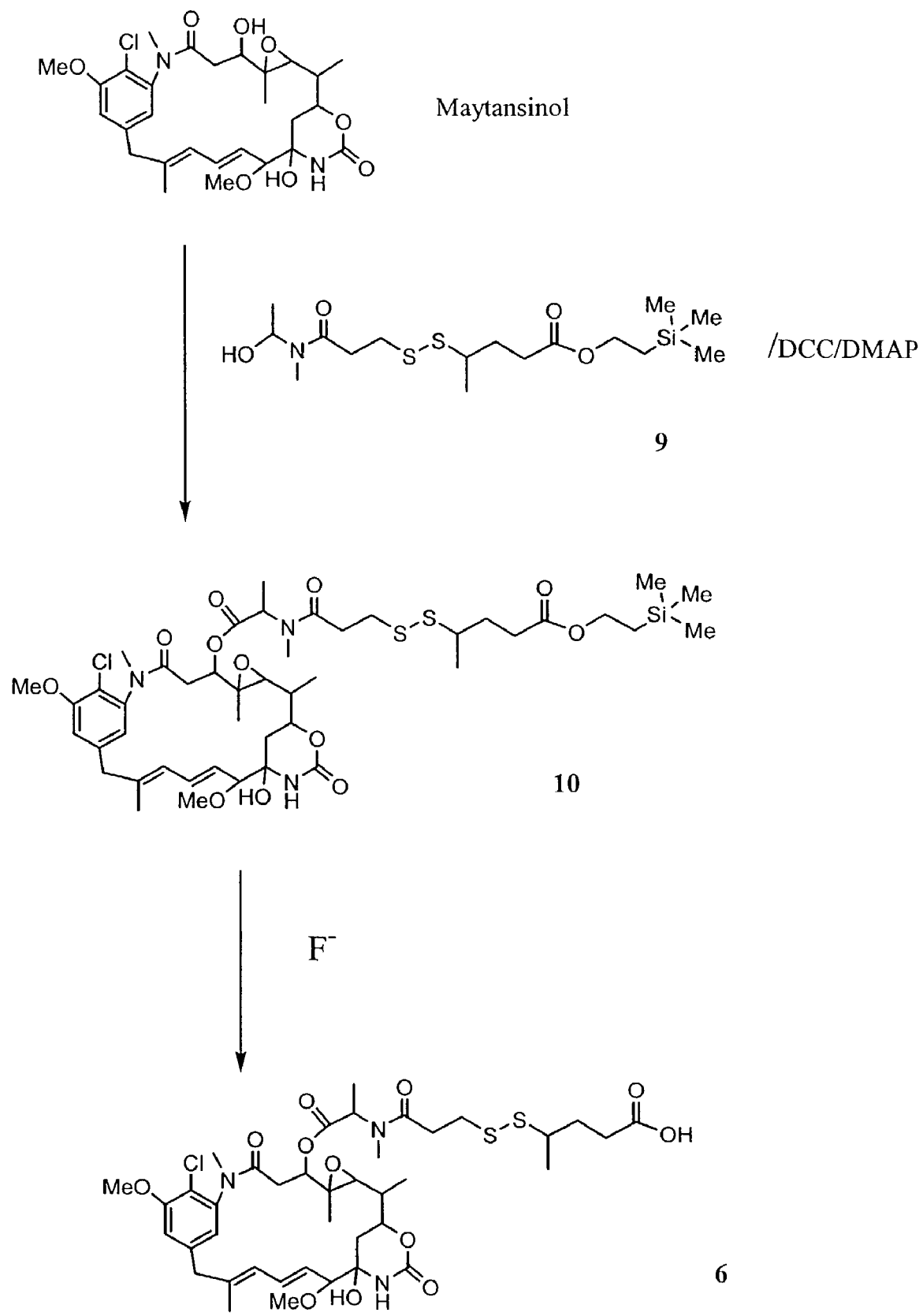
FIG. 5 shows an alternative pathway for the production of L-DM1-TPA (compound 6).

Maytansinoid 6 can also be directly prepared from maytansinol as outlined in FIG. 5. Compound 9 is prepared by disulfide exchange between the (2-trimethylsilyl)ethyl ester of PPA (5) and N-methyl-N-(3-mercapto-1-oxopropyl)-L-alanine. The product can be purified by column chromatography on silica gel. Esterification of maytansinol with 6 equivalents of 9 in the presence of DCC (7.2 eq) and dimethylaminopyridine (DMAP) or zinc chloride (1 eq) in dichloromethane, as previously described (U.S. Pat. No. 5,208,020) gives maytansinoid 10, which can be purified by standard chemical means, such as silica gel chromatography or HPLC. Treatment of 10 with 5 equivalents of tetrabutylammonium fluoride in tetrahydrofuran for 30 min. at room temperature results in cleavage of the (trimethylsilyl)ethyl protecting group to yield 6, which can be purified by HPLC as described in Example 2a.

Example 5

Evaluation of huN901-DM1 Conjugates for In Vitro Potency

The huN901-DM1 conjugates prepared by this new, one step method were evaluated for in vitro cytotoxicity towards antigen-expressing cells as follows. A clone of A431 cells constitutively expressing the antigen for huN901 (NCAM/CD56) were used in this assay. Cells were plated into 6-well tissue-culture treated plates at a density of $2 \times 10^3$ cells/well in 2 ml of DMEM medium supplemented with 10% fetal calf serum and penicillin+streptomycin. A huN901-DM1 conjugate or the control huN901 antibody was added to the wells at the time of plating, and the cultures were incubated in a tissue culture incubator at 37° C., 6% $CO_2$, for 5 to 7 days to form colonies not smaller than 25 cells/colony. The plates were then washed with PBS, and then fixed/stained for 30 min at room temperature with 10% formaldehyde/0.2% (w/v) Crystal Violet in PBS. The wells were rinsed 3 times with water, dried by air, and the colonies were counted under a dissection low magnification microscope. The surviving fractions were calculated as the number of colonies in drug-treated well/number of colonies in non-treated well.

The results (FIG. 1) indicate that huN901-DM1 conjugates prepared by the one-step method using maytansinoid 2, followed by purification either by Sephadex G25 or Sephacryl S300 chromatography were potent in killing antigen positive cells, with an $IC_{50}$ value of $1 \times 10^{-10}$ M. In contrast, the unconjugated huN901 antibody was non-toxic.

What is claimed is:

1. A method for producing a cytotoxic conjugate, said method comprising incubating a cell binding agent having an amino group with one or more N-methyl-alanine- or N-methyl-cysteine-containing maytansinoid molecules that has, on the N-methyl-alanine or N-methyl-cysteine group, a disulfide moiety that bears a reactive ester, whereby the amino group of the cell binding agent is linked to one or more of said maytansinoid molecules via reaction with the reactive ester essentially in a single step.

2. A method for producing a cytotoxic conjugate, said method comprising incubating a cell binding agent having an amino group with one or more N-methyl-alanine- or N-methyl-cysteine-containing maytansinoid molecules that has, on the N-methyl-alanine or N-methyl-cysteine group, a disulfide moiety that bears a reactive ester, whereby the amino group of the cell binding agent is linked to one or more of said maytansinoid molecules via reaction with the reactive ester essentially in a single step, and wherein said cell binding agent is one that has not been previously modified to bear a reactive group for use in conjugation with said one or more maytansinoid molecules.

3. The method according to claim 1 or 2, further comprising a second step of isolating the conjugate.

4. The method according to claim 1 or 2, wherein said reactive ester is a N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl ester.

5. The method according to claim 1 or 2, wherein said reactive ester is a N-succinimidyl ester.

6. The method according to claim 1 or 2, wherein said reactive ester is a N-sulfosuccinimidyl ester.

7. The method according to claim 1 or 2, wherein said cell binding agent is selected from the group consisting of monoclonal antibodies, polyclonal antibodies, antibody fragments, lymphokines, hormones, growth factors, vitamins and nutrient-transport molecules.

8. The method according to claim 1 or 2, wherein said cell binding agent is a monoclonal antibody.

9. The method according to claim 1 or 2, wherein said cell binding agent is an antibody fragment.

10. The method according to claim 1 or 2, wherein said disulfide moiety that bears a reactive ester is represented by the following formula:

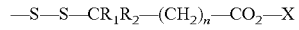

wherein $R_1$ and $R_2$ are each independently H or linear or branched alkyl, n is 1-5, and X is a part of an active ester.

11. The method according to claim 10, wherein X is N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl or 3-carboxy-4-nitrophenyl.

12. The method according to claim 10, wherein $R_1$ and $R_2$ are each independently H, propyl, butyl, pentyl, hexyl, isopropyl, isobutyl, sec.-butyl, tert.-butyl, isopentyl or 1-ethyl-propyl.

13. The method according to claim 11, wherein $R_1$ and $R_2$ are each independently H, propyl, butyl, pentyl, hexyl, isopropyl, isobutyl, sec.-butyl, tert.-butyl, isopentyl or 1-ethyl-propyl.

14. The method according to claim 10, wherein said cell binding agent is a monoclonal antibody.

15. The method according to claim 11, wherein said cell binding agent is a monoclonal antibody.

16. The method according to claim 10, wherein said cell binding agent is an antibody fragment.

17. The method according to claim 11, wherein said cell binding agent is an antibody fragment.

* * * * *